United States Patent
Foucault et al.

(10) Patent No.: US 12,421,464 B2
(45) Date of Patent: Sep. 23, 2025

(54) PRODUCTION OF SYNTHESIS GAS FROM GASIFYING AND REFORMING CARBONACEOUS MATERIAL

(71) Applicant: ENERKEM INC., Montreal (CA)

(72) Inventors: Maxime Foucault, Montreal (CA); Jean-Pierre Crete, Montreal (CA); Guillaume Drolet, Montreal (CA); Micael Boulet, Montreal (CA); Louis Denomme, Montreal (CA); Boris Valsecchi, Montreal (CA)

(73) Assignee: ENERKEM INC., Montreal (CA)

( * ) Notice: Subject to any disclaimer, the term of this patent is extended or adjusted under 35 U.S.C. 154(b) by 991 days.

(21) Appl. No.: 17/599,685

(22) PCT Filed: Apr. 9, 2020

(86) PCT No.: PCT/CA2020/050464
§ 371 (c)(1),
(2) Date: Sep. 29, 2021

(87) PCT Pub. No.: WO2020/206538
PCT Pub. Date: Oct. 15, 2020

(65) Prior Publication Data
US 2022/0195320 A1    Jun. 23, 2022

Related U.S. Application Data

(60) Provisional application No. 62/833,158, filed on Apr. 12, 2019.

(51) Int. Cl.
*C10J 3/76* (2006.01)
*B07B 13/11* (2006.01)
(Continued)

(52) U.S. Cl.
CPC ........ *C10J 3/76* (2013.01); *C01B 3/36* (2013.01); *C07C 69/14* (2013.01); *C10J 3/482* (2013.01);
(Continued)

(58) Field of Classification Search
CPC .................................................. B07B 13/11
See application file for complete search history.

(56) References Cited

U.S. PATENT DOCUMENTS 8,080,693 B2    12/2011    Chornet et al.
8,137,655 B2 †   3/2012    Chornet
(Continued)

FOREIGN PATENT DOCUMENTS

EP    0676465         10/1995
EP    0676465 A1 †   10/1995
(Continued)

OTHER PUBLICATIONS

Jean-Michel Lavoie et al. "Conversion of NOn-Homogeneous Biomass to Ultraclean Syngas and Catalytic Conversion to Ethanol"; Biofuel's Engineering Process Technology;2011; pp. 333-352.
(Continued)

*Primary Examiner* — Peter F Godenschwager
(74) *Attorney, Agent, or Firm* — Norton Rose Fulbirght Canada

(57) ABSTRACT

It is provided a method of converting a carbonaceous material into syngas at a carbon conversion rate of at least 78% comprising gasifying the carbonaceous material in a fluidized bed reactor producing a crude syngas, classifying the crude syngas by particle size and density into a cut sizing device, introducing the classified particle crude syngas into a thermal reformer and reforming the classified crude syngas at a temperature above mineral melting point, producing the syngas.

18 Claims, 5 Drawing Sheets

(51) Int. Cl.
 *C01B 3/36* (2006.01)
 *C07C 69/14* (2006.01)
 *C10J 3/48* (2006.01)
 *C10K 3/00* (2006.01)

(52) U.S. Cl.
 CPC ............... *C10K 3/005* (2013.01); *B07B 13/11* (2013.01); *C01B 2203/0205* (2013.01); *C01B 2203/0255* (2013.01); *C01B 2203/061* (2013.01); *C01B 2203/1258* (2013.01); *C10J 2300/092* (2013.01); *C10J 2300/0923* (2013.01); *C10J 2300/0946* (2013.01); *C10J 2300/0956* (2013.01); *C10J 2300/0959* (2013.01); *C10J 2300/0976* (2013.01); *C10J 2300/1625* (2013.01); *C10J 2300/1665* (2013.01)

(56) References Cited

U.S. PATENT DOCUMENTS

| | | |
|---|---|---|
| 2010/0040510 A1 | 2/2010 | Randhava et al. |
| 2010/0224835 A1 | 9/2010 | Chornet et al. |
| 2013/0143972 A1 | 6/2013 | Townsend et al. |
| 2015/0275112 A1 | 10/2015 | Boissonnet et al. |

FOREIGN PATENT DOCUMENTS

| | | |
|---|---|---|
| JP | H08500389 | 1/1996 |
| JP | 2010132902 | 6/2010 |
| JP | 2011208003 | 10/2011 |
| JP | 2012512282 | 5/2012 |
| JP | 2013046893 | 3/2013 |
| JP | 2016505666 | 2/2016 |

OTHER PUBLICATIONS

Lavoie, Jean-Michel, Stéphane Marie-Rose, and David Lynch. Non-homogeneous residual feedstocks to biofuels and chemicals via the methanol route. Biomass Conversion and Biorefinery 3 (2013): 39-44.†

Shah, M. and Larry Bool. "Hot Oxygen Burner (HOB) Technology for Syngas Generation." 2018 Global Syngas Technologies Conference, Colorado Springs, CO, Oct. 29, 2018.†

† cited by third party

PRODUCTION OF SYNTHESIS GAS FROM GASIFYING AND REFORMING CARBONACEOUS MATERIAL

CROSS-REFERENCE TO RELATED APPLICATIONS

The present application is claiming priority from U.S. Provisional Application No. 62/833,158 filed Apr. 12, 2019, the content of which is hereby incorporated by reference in its entirety.

TECHNICAL FIELD

It is provided a method of converting a carbonaceous material into synthesis gas comprising gasifying the carbonaceous material, classifying the crude syngas by particle size and density, and reforming the classified crude syngas.

BACKGROUND

Synthesis gas, also called syngas, is a fuel gas mixture comprising primarily of carbon monoxide (CO), carbon dioxide ($CO_2$) and hydrogen ($H_2$). When it is a desired product, it may also be comprised of methane ($CH_4$) by changing operating temperature.

Syngas can be produced from many sources, including biomass, or virtually any carbonaceous material, by reaction with steam (steam reforming), carbon dioxide (dry reforming), air (partial oxidation), oxygen (partial oxidation) or any mixture of the reactants listed. Syngas is a crucial intermediate resource for production of hydrogen, ammonia, and methanol for example. Utilisation of syngas in internal combustion engines and in as a renewable energy resource is an ongoing, extensive investigation.

Carbonaceous material refers to any gas, liquid or solid that contains the "Carbon" atom. In most cases, these atoms may be originated from plants or animals and their derivatives, or from fossil fuel and its derivatives. Examples of carbonaceous materials include, but are not limited to, Municipal Solid Waste (MSW); Industrial, Commercial, and Institutional waste (IC&I); Construction and Demolition waste (C&D); any petroleum product; plastic; homogenous and/or non-homogeneous biomass.

Converting carbonaceous materials and waste into synthesis gas can be achieved with gasification techniques. Syngas may be produced by gasifying carbonaceous feedstock. The gasification provides a crude syngas which includes impurities such as ammonia ($NH_3$), sulfur (as hydrogen sulfide ($H_2S$) and carbonyl sulfide (COS)), chlorine (as HCl), volatile metals, aromatic tars (NBTX; naphthalene, benzene, toluene and xylene), tars (including HAP), fines ashes (in the form of particles containing metals and metal salts), bed material, and char (solid particulates typically above 0.001 mm and containing metals, salts and mostly carbon). Such impurities, however, limit the ability of the syngas to be used as a fuel or to be employed in the synthesis of other useful materials without a cleaning process.

For example, when syngas is used to produce methanol, the syngas reacts under pressure in the presence of a catalyst. The impurities in a crude syngas produced as a result of gasifying carbonaceous feedstock may poison or deactivate the catalyst.

There are many types of gasifier apparatus that already exist and are used in various processes, including plasma assisted gasification, staged gasification and/or indirect gasification processes. Other examples include fixed bed, moving bed, fluidized bed, circulating fluidized bed and entrained-flow gasifiers. The entrained-flow gasifier typically works at a higher outlet temperature than the other gasifiers. It produces a syngas with less residual char and tar than any other type of gasifier and melts the feedstock mineral material into a glass-like material. One drawback of the entrained-flow gasifier is the limitation in the solid material feeding preparation. Two forms of feed are generally employed in entrained-flow gasifiers; either very fine particle injection with a conveying gas (pneumatic conveying) or mechanical device, or injection of a liquid-solid slurry made of very fine solids.

Untreated waste and many untreated biomass materials require extensive grinding and/or pretreatment to achieve a fine particle feed size. In addition, most types of waste, biomass, non-coal like carbonaceous solid materials and/or very low density materials produce a fluffy feed instead of finely divided particles. It is accepted that waste and biomass can undergo a shredding and/or grinding process that produces coarse sized particles, many orders of magnitude bigger than those required for an entrained-flow gasifier.

Another issue with the entrained-flow gasifier is the low residence time in the reactor, consisting of a few seconds to less than a second. This requires a narrow lower range of feedstock particle size/density distribution, otherwise the conversion efficiency to syngas of such feedstock would be low, resulting in the production of more undesirable char and tar in the produced syngas.

When the feed consists in "hard to finely grind" carbonaceous feedstock, clumps, strings, hair-like fibers and/or lints are produced, which result in broadening the particle size distribution and decreases the homogeneity of the particle size/density distribution. Such decreases in homogeneity results in unhomogenized feed and reduced conversion efficiency in the entrained-flow gasifier.

In addition, fluidized bed and, to a certain extent, circulating fluidized bed gasifiers are well known to be able to handle heterogeneous particle size feed, ranging from millimeters to centimeters, avoiding the feedstock grinding problem of the entrained-flow gasifier. Depending on the mineral content of the feedstock and particularly the alkali content, softening of those components happens between 750 to 900° C. This creates agglomeration with and within the fluidization media, forcing operating those types of gasifiers at lower temperature to avoid the softening range regime. Indeed, except the entrained-flow gasifier, all the other types of gasification systems operate at relatively low syngas outlet temperatures, generating a considerable amount of char and tar and reducing the overall carbon conversion into syngas.

A major challenge with carbonaceous materials from waste and biomass compared, for example, to coal gasification is the amount, type, and variability of alkalis and inerts present in the feedstock. Waste and biomass carbonaceous materials contain a wide variety of alkalis and the amount is often more than one order of magnitude larger than with coal feedstock. These alkalis are well known to be aggressive on traditional thick refractory materials used in entrained-flow gasifier designs. In consequence, thick refractory lined entrained-flow gasifiers used for coal gasification need to be changed every one to two years. It is estimated that with waste and biomass, the same refractory design would last less than a few months, increasing unsustainably the operating cost and decreasing plant operational availability.

Alternatively, an entrained-flow gasifier can also come with a cooling wall membrane design, also known as "membrane wall design". It consists of a water tube pipe that is shaped to form the reactor high temperature reaction zone. On the interior surface side of this high temperature zone, there are many studs and a relatively thin layer of refractory lining. The cooling wall membrane cools the inner refractory surface of the reactor and freezes in place some of the melted mineral, protecting the cooling wall membrane from the liquid melted mineral that flows on top of the frozen layer. This type of gasifier is used in the coal industry. However, it is designed for a narrow range of inert mineral particle diameter. Bigger particles such as those that come from waste of biomass, do not have the time and only partially melt creating a mixture of fully melted mineral with unmelted mineral solid particles. This mixture has poor and highly variable flow properties resulting in difficulties in evacuating the mineral from the reactor, and increasing the risk of blocking the tapping orifice or other removal equipment.

Contrary to coal feedstocks which have a relatively narrow range of particle density/size, biomass, waste and mixtures of both have a very broad range of particle diameter and bulk density. As can be seen from Table 1, for a same mass, the particle size of different biomass, waste and aggregate can result into a particle apparent diameter ratio ranging about from 1 up to 800. If one would sieve such a broad range of material to a specific particle size diameter, particles having the same diameter would range in mass ratio from 1 to 800. Feeding such a range of feedstock density into an entrained-flow gasifier creates heterogeneity in the carbon to syngas efficiency and worsens the solid/melted mineral particle problem described herein. Thus, entrained-flow gasifiers can operate at high temperatures and handle melted mineral only when the particle size is small, in the micron range, and when the mass, particle size distribution, and residual mineral content is uniform.

TABLE 1

Average typical density of different material

| Material | Density (kg/m$^3$) |
| --- | --- |
| Expanded polystyrene | 11 |
| Poly-film floc (plastic film fluff) | 32 |
| Ground cork | 80 |
| RDF fluff | 100 |
| MSW fluff | 175 |
| Wood chip | 320 |
| Wood pellet | 450 |
| Ground coal | 640 |
| Tar | 1150 |
| Sand & gravel | 1750 |
| Alumina grain density | 3000 |
| Copper grain density | 8960 |
| Bronze shot | 9440 |

U.S. Pat. No. 8,137,655 describes a method to gasify carbonaceous material into a fluidized bed with a secondary reforming process into the freeboard and/or a separate vessel, debottlenecking the fluid bed softening point temperature limit of 750° C. to 900° C. One of the issues observed with the process described therein is the limitation of a second temperature limit consisting of a liquefaction temperature limit that creates droplets of liquid mineral that can agglomerate on the gasifier wall and exhaust pipe of the freeboard. Depending on the nature of the mineral and alkalis fed, this second temperature limit is in the range of 900° C. to 1100° C. In U.S. Pat. No. 8,137,655, reforming was performed to at most 1200° C., mainly at about 1000° C. Above these temperatures, the gasifier needs to be designed to handle melted mineral, such as an entrained-flow gasifier with its limitation as described hereinabove.

U.S. Pat. No. 5,900,224 discloses a method for treating wastes by gasification using a revolving-type fluidized-bed reactor followed by a swirling-type high-temperature combustor to produce a syngas and reacting the syngas CO and $H_2O$ with water gas shift reaction to $CO_2$ and $H_2$ and removing the $CO_2$ for ultimately synthesizing ammonia. This method, while focusing on $H_2/NH_3$ production and not $H_2$, CO and $CO_2$, does not perform an operation or have a device to optimize conversion of carbon and mineral melting that considers problems associated with the wide range of density and size of the particles described hereinabove. Moreover, there is no mention or teaching of means that would allow handling feedstock with high alkali content.

Considering the actual available technologies, it is not possible to gasify carbonaceous materials that are course to finely ground with a high carbon to syngas conversion efficiency.

There is thus still a need to be provided with a means and/or process for the gasification of course to finely grind carbonaceous materials with high conversion of carbon to syngas while creating a syngas with very low char and tar residual, and while handling the melted mineral.

SUMMARY

One aim of the present disclosure is to provide a method of converting a carbonaceous material into synthesis gas comprising gasifying the carbonaceous material in a fluidized bed, producing a crude syngas; classifying the crude syngas by particle aerodynamic velocity into a cut sizing device producing a classified crude syngas; introducing the classified particle crude syngas into a thermal reformer/entrained flow gasifier, and reforming said classified crude syngas at a temperature above mineral melting point, producing the synthesis gaz.

In an embodiment, the cut sizing device is a freeboard enlargement, a cyclone, a perforated shroud, a helical strakes, a longitudinal slats, a filter, a cascade impactor, an aerodynamic classifier or any combination thereof.

In another embodiment, the carbonaceous material is fed to the fluidized bed reactor by a feeding system.

In a further embodiment, the fluidized bed reactor comprises a fluidized bed material selected from the group consisting of alumina, limestone, dolomite, sand, olivine, anthracite, desulfurized petroleum coke or a combination in any proportion thereof.

In another embodiment, a fluidizing agent is used to heat up the fluidized bed reactor and is fed oxygen to assist in gasification of the carbonaceous material.

In an embodiment, the fluidizing agent is air, oxygen, carbon dioxide, nitrogen, steam or any combination in any proportion thereof.

In another embodiment, the carbonaceous material is gasified at a temperature of about 450° C. to about 800° C.

In an embodiment, the carbonaceous material is gasified at a temperature of about 500° C. to about 700° C.

In a further embodiment, the classified particle crude syngas is reformed in a thermal reformer.

In a further embodiment, the reforming operating temperature is of about 1200° C. to about 2000° C.

In another embodiment, air, oxygen, carbon dioxide, nitrogen, steam or any combination in any proportion thereof is fed to the reformer to increase the temperature of the reformer.

In another embodiment, the classified crude syngas is reformed at a temperature of about 1200° C. to about 1800° C.

In an embodiment, the reformer comprises a cooling wall membrane.

In another embodiment, the cooling wall membrane is made of studded pipes.

In a further embodiment, the carbonaceous material is converted into syngas with at least 78% of carbon conversion rate, preferably with at least 90% of carbon conversion rate, more preferably with at least 96% of carbon conversion rate.

In an embodiment, the carbonaceous material is a liquid, a solid and/or a gas containing carbon.

In an embodiment, the carbonaceous material is a biomass.

In another embodiment, the biomass is a homogeneous biomass, a non-homogenous biomass, a heterogeneous biomass, urban biomass, or a combination thereof.

In an embodiment, the homogenous biomass is from a coniferous tree, a deciduous tree, an agricultural material, a primary sludge, waste cooking oil, lychee fruit bark or stillage.

In another embodiment, the non-homogenous biomass is from mixed forest residues, or mixed tree residues.

In a further embodiment, the carbonaceous material wherein the carbonaceous material comprises a plastic, a metal, an inorganic salt, an organic compound, industrial wastes, recycling facilities rejects, automobile fluff, municipal solid waste, ICI waste, C&D waste, refuse derived fuel (RDF), solid recovered fuel, sewage sludge, used wood utility poles, wood railroad ties, wood, tire, synthetic textile, carpet, synthetic rubber, materials of fossil fuel or petrochemical origin, expanded polystyrene, poly-film floc, construction wood material, or any combination thereof.

It is also provided a method of converting a carbonaceous material into a chemical comprising gasifying the carbonaceous material in a fluidized bed, producing a crude syngas; classifying the crude syngas by particle aerodynamic velocity into a cut sizing device producing classified crude syngas; introducing said classified particle crude syngas into a thermal reformer; reforming said classified crude syngas at a temperature above mineral melting point, producing the synthesis gas; and converting said synthesis gas into methanol in a methanol reactor, producing methanol.

In an embodiment, the method further comprises the steps of reacting the methanol with carbon monoxide (CO) in a carbonylation reactor to methyl acetate; feeding the methyl acetate into an hydrogenolysis reactor and reacting the methyl acetate with hydrogen ($H_2$) producing ethanol, methanol, ethyl acetate or a combination thereof.

BRIEF DESCRIPTION OF THE DRAWINGS

Reference will now be made to the accompanying drawings.

DETAILED DESCRIPTION

It is provided a method for preparing, treating and converting carbonaceous materials into suitable syngas with high carbon to syngas conversion rate. In order to achieve this objective, the method comprises gasifying carbonaceous materials to form crude syngas in a fluidized bed gasifier at a temperature low enough to avoid agglomeration problems. Crude syngas is the syngas created while gasifying at low temperature. It comprises syngas with the addition of char, bed material, mineral matter particle, tar and many gaseous, liquid and solid petroleum type products. Afterwards, the crude syngas is conveyed from the fluidized bed zone to a cut sizing device by fluidization entrainment.

Figure 1:
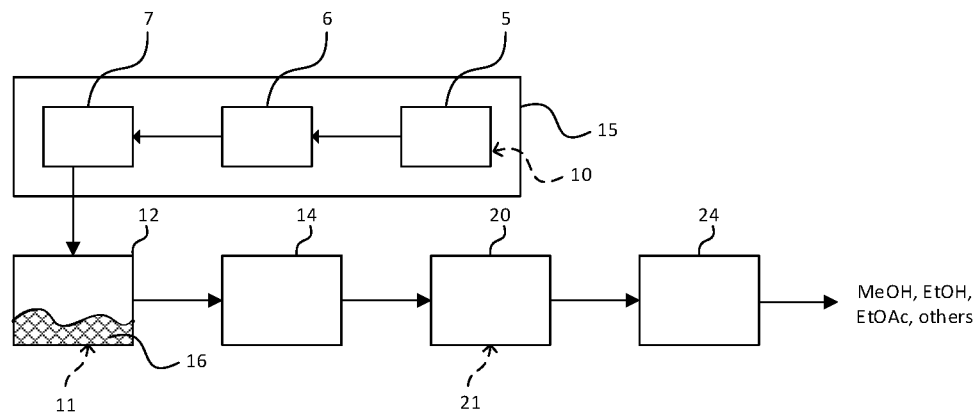
FIG. 1 illustrates a block diagram view of the process of producing syngas.

As illustrated in FIG. 1, the carbonaceous material 10 is introduced in the fluidized bed gasifier 16 with the help of the feeding system 15. The gasifier 12 converts the carbonaceous material 10 into crude syngas using fluidizing agent 11. The crude syngas, which includes a broad range of particle diameter/density, is introduced into a cut sizing device 14 that sorts particles to suit the design of the crude syngas thermal reformer 20. The classified crude syngas and oxidizing agent 21 are introduced into the crude syngas thermal reformer 20 at high temperature to reform the crude syngas into a reformed syngas mainly composed of $H_2$, CO, $CO_2$, $H_2O$ and other compounds in small concentration. The reformed syngas undergoes a stage of water and/or chemical and/or physical scrubbing 24 to remove contaminants to produce a clean syngas for further use as fuel, power generation, alcohol synthesis (MeOH, DME, EtOH and others), hydrocarbon synthesis and others uses.

Also encompassed is the formation of other products from syngas as described herein, such as for example, Fischer-Tropsch fuel, Fischer-Tropsch to Olefins (FTO) synthesis.

In the embodiment, the carbonaceous material 10 is fed through a system consisting of three steps; pressurization 5, flow control 6 and feeding 7 to the gasifier 12. Each step can be performed from different equipment. As an example, typical types of equipment used are a lock-hopper, a conveyor and/or a screw.

The fluidized bed 16 comprises an appropriate fluidized bed material, such as for example, but not limited to, alumina, limestone, dolomite, sand, olivine, anthracite, desulfurized petroleum coke and any combination in any proportion thereof.

A fluidizing agent 11, composed of air, oxygen, carbon dioxide, nitrogen, steam or any combination in any proportion thereof is conveyed into the gasifier 12. Air is usually used for the start-up, to heat up the gasifier, and oxygen-steam are usually used during normal operation thereby minimizing the nitrogen content and syngas dilution effect for downstream catalytic conversion. The fluidizing agent can be preheated, such as for example to a temperature at or below bed temperature to minimize steam condensation and also to promote higher syngas yield in the gasifier 12. The final oxidant concentration is adjusted on temperature control to maintain the gasifier fluid bed temperature (e.g. between 450° C. and 800° C.).

In an embodiment, the fluidized bed gasifier 12 is operated at about 650° C. and from 0.1 to 70 barg. In another embodiment, the gasifier 12 is operated at a temperature that does not exceed 750° C. and at a pressure that does not exceed 10 barg. In a non-limiting embodiment, the material 10 is gasified at a temperature which does not exceed 725° C. In another non-limiting embodiment, the material 10 is gasified at a temperature which does not exceed 700° C. In a non-limiting embodiment, the material 10 is gasified at a pressure which does not exceed 4 barg.

The temperature is set to avoid salt melting/agglomeration within the bed that occurs slightly above this point and to allow good thermal conversion and devolatilization of carbonaceous material into crude syngas. The overall reaction can be expressed as:

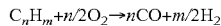

$$C_nH_m + n/2 O_2 \rightarrow nCO + m/2 H_2$$

Accordingly, this reaction represents the global exothermic reaction to produce CO and $H_2$. Oxidation reactions are required to supply the heat for compensating endothermic reaction/transformation such as water evaporation and others. This means that some $CO_2$ and $H_2O$ are also generated by oxidation reactions. Other minor reactions occur with other elements present in the material 10, such as chlorine that generates HCl and sulfur that produces $H_2S$ and COS. HCN, $N_2$ and $NH_3$ are also formed when nitrogen is present in the material 10.

Figure 2:
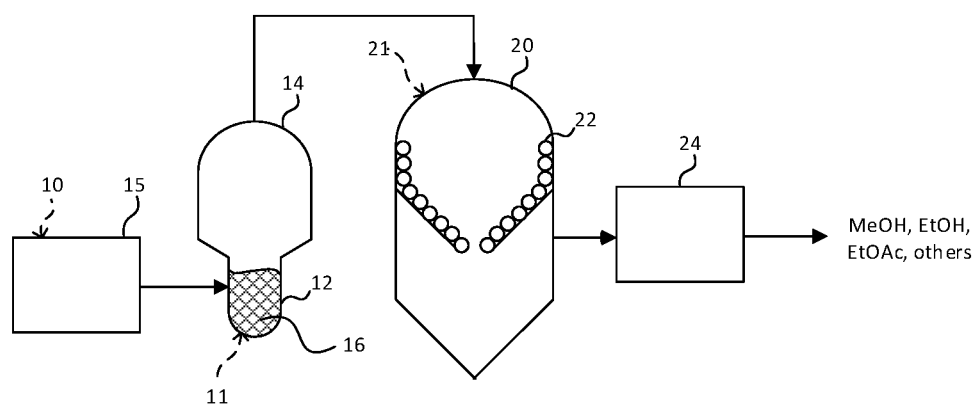
FIG. 2 illustrates a schematic view of the process of producing syngas in accordance to an embodiment.

The fluidized bed gasifier 12 as described herein and illustrated in FIG. 2 comprises a cut sizing device 14. The cut sizing device 14 consists of a freeboard zone of the gasifier 12. In an embodiment, the design of the freeboard zone shape is adjusted in such a manner that particles entrained from the bed zone 16 are classified by density, particle size and shape. The freeboard, driven by its enlarged diameter, will act as an aerodynamic particle cut sizing device. As encompassed herein, the cut sizing device can be a freeboard enlargement, a cyclone, a perforated shroud, a helical strakes, a longitudinal slats, a filter, a cascade impactor, an aerodynamic classifier or any combination thereof.

Figure 4:
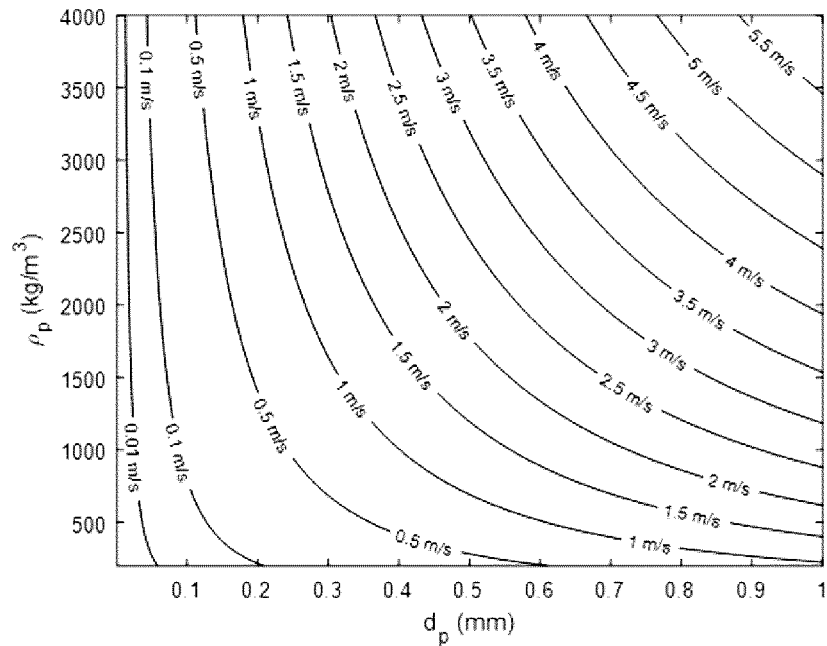
FIG. 4 present terminal velocity iso-curve of particles having different diameter and density.

Big particles with low density having an aerodynamic terminal velocity smaller than the actual velocity of the cut sizing device will be entrained. Small particles with very high density having aerodynamic terminal velocity larger than the actual cut sizing device actual velocity will not be entrained and will drop back into the fluidized bed 16 for further gasification. For a specific particle shape, FIG. 4 presents the iso-curves of aerodynamic terminal velocity for different values of diameter and density, illustrating the separation effect of any aerodynamic cut sizing device. Separation is not based only on particle size or mass, it is a combination of the particle size, mass and shape. A bigger porous particle with low density may be entrained as a highly dense small particle could fall back in the fluidizing bed. This aerodynamic cut sizing device is adjusted to match the desired cut size/density/shape needed to maximize the carbon conversion efficiency of the subsequent steps.

Figure 5:
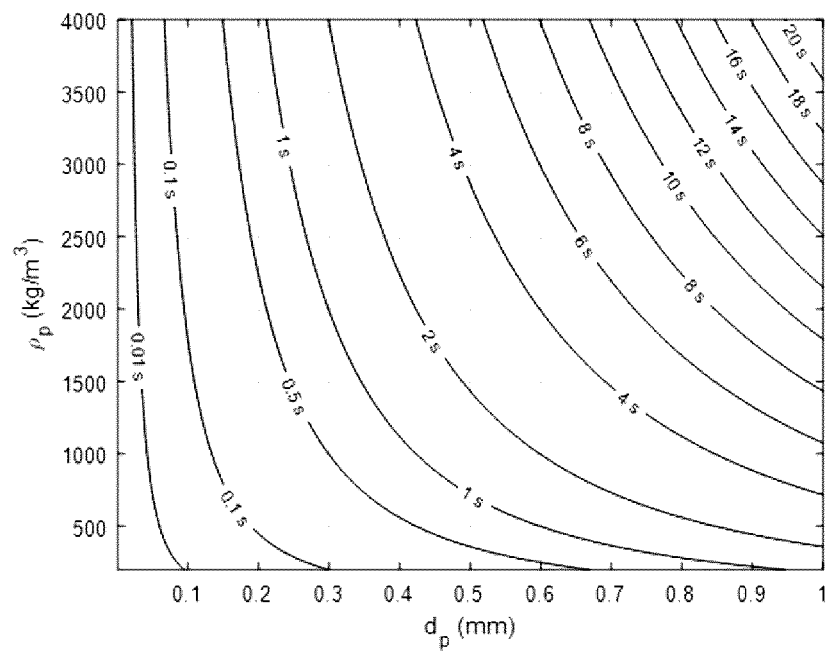
FIG. 5 present, for a specific set of operating condition, residence time iso-curve needed to fully convert to syngas a char particle of different diameter and density.

For specific operating parameters and particle types, FIG. 5 presents time iso-curves needed to fully convert carbon containing particle to syngas within a crude syngas thermal reformer. In this graphic, for any iso-curve, any particle that would be located left and/or below the curve would be fully converted. As illustrated, the conversion time needed is not only proportional on particle diameter or density, but on a combination of diameter and density. This shows the need to condition the particle entrained with the crude syngas to achieve a cut classified crude syngas that increases the carbon conversion rate.

Figure 6:
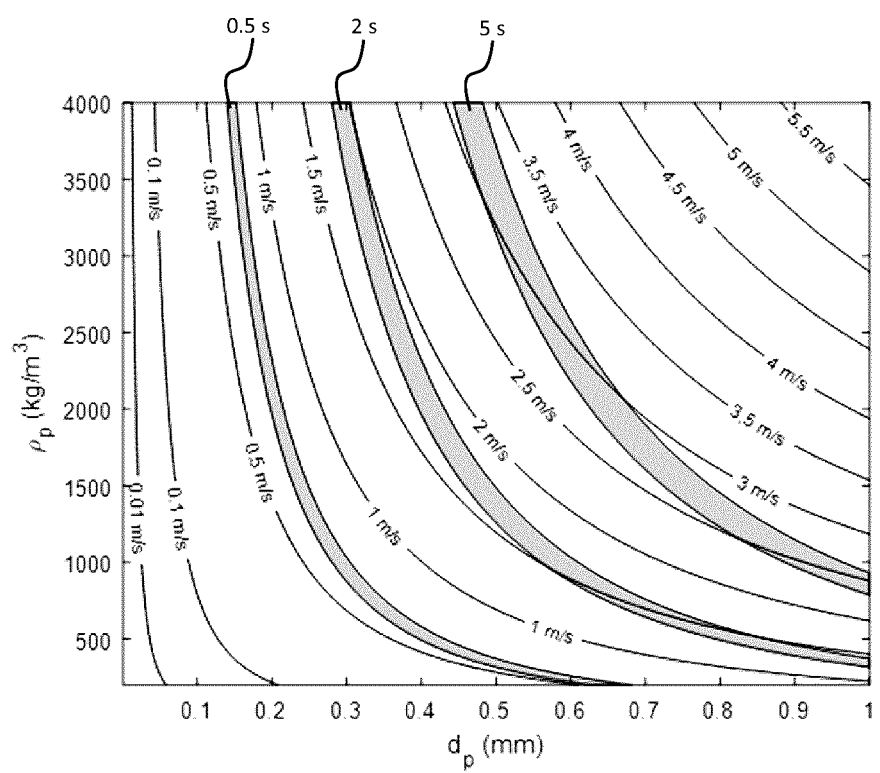
FIG. 6 presents a superposition of FIG. 5 at different operation temperatures and residence times of 0.5, 2 and 5 sec over the FIG. 6.

For specific operating parameters and particle types, FIG. 6 presents a concatenation of FIG. 5 over FIG. 4. The wide grey stripe represents crude syngas thermal reformer conversion time of 0.5, 2 and 5 seconds (s) for a range of high temperature operating setpoint and for different particle diameter and density. The iso-curve represents the aerodynamic terminal velocity for different diameter and density. As illustrated, both conversion curve in seconds and aerodynamic terminal velocity in m/s closely match for any given diameter and density. As an example, a design of reformer having a residence time of 0.5 seconds would have a higher conversion to reformed syngas when an aerodynamic cut sizing device is added to retain in the fluidizing bed particles with an aerodynamic terminal velocity higher than 0.5 m/s. This allows a particle with 0.4 mm in diameter and 500 kg/m$^3$ to be fully converted as well as a particle of 0.2 mm in diameter and 1500 kg/m$^3$. A particle of 0.4 mm in diameter and 1500 kg/m$^3$ falls back in the bed, preventing a too large/dense particle from entering the crude syngas thermal reformer and thus not being fully converted.

The classified crude syngas is then introduced into a syngas thermal reformer 20. The syngas thermal reformer 20 is designed to operate at high temperature above the inert and salt softening point, to handle melted mineral and to discharge this melted mineral into a cooling zone for its extraction.

The classified crude syngas then flows to the syngas thermal reformer 20 where pure oxygen 21 is fed in the upper part of the reformer 20, thereby increasing the temperature above mineral melting point, usually >1200° C., and enhancing thermal conversion of the heavy tars, char, aromatics and methane and alike into additional CO and $H_2$. In an embodiment, air, oxygen, carbon dioxide, nitrogen, steam or any combination in any proportion thereof is fed to the reformer to increase the temperature of the reformer.

Figure 3:
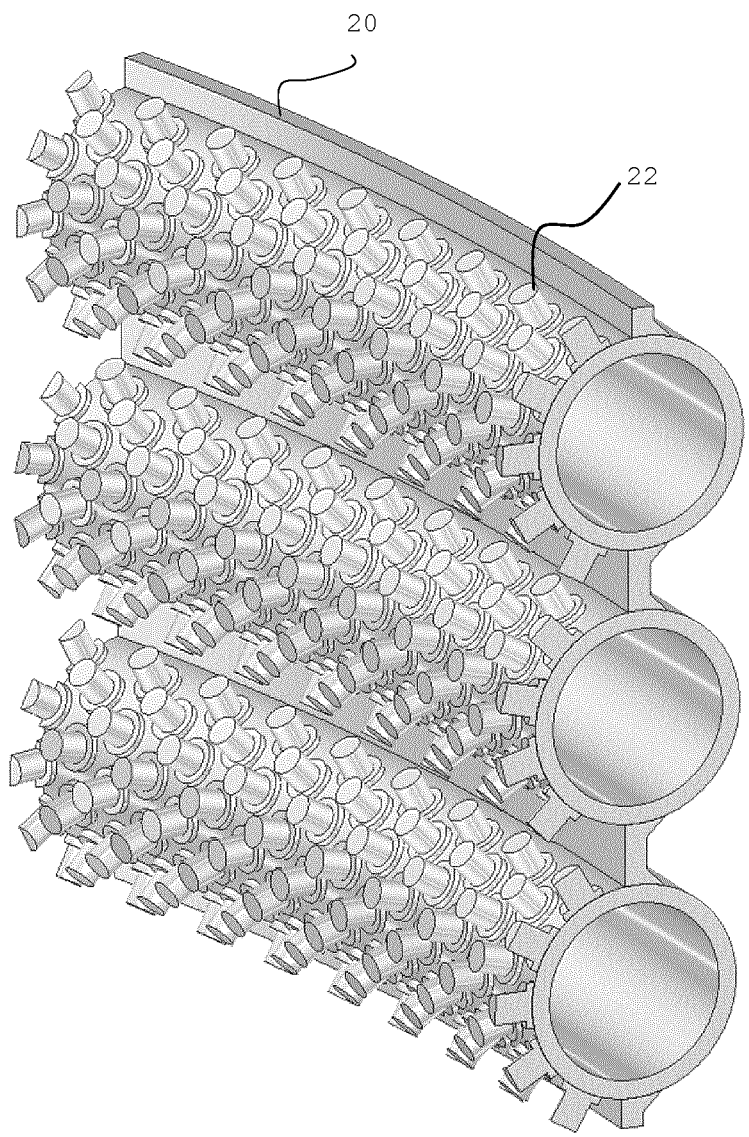
FIG. 3 is an illustration of the studs on the surface of the cooling wall membrane of the reformer as described herein.

The entrained solids melt at the reformer's 20 operating temperatures and they are entrained as fine droplets in the syngas and accumulated on the wall by creating a film of molten materials slowly flowing on an external layer of solidified materials. As illustrated in FIG. 3, in an embodiment, the reformer 20 described herein comprises a cooling wall membrane made of studded cooling pipes 22. At this stage, both the hot syngas mixture and the molten solids are corrosive, and the mentioned formation of a solid layer on the wall of the reformer acts as a protective barrier. In an embodiment, the layer is maintained by means of circulating high-pressure boiler water in the cooling wall membrane 22, thus providing sufficient cooling to the first layer to keep it in the solid form.

Figure 7:
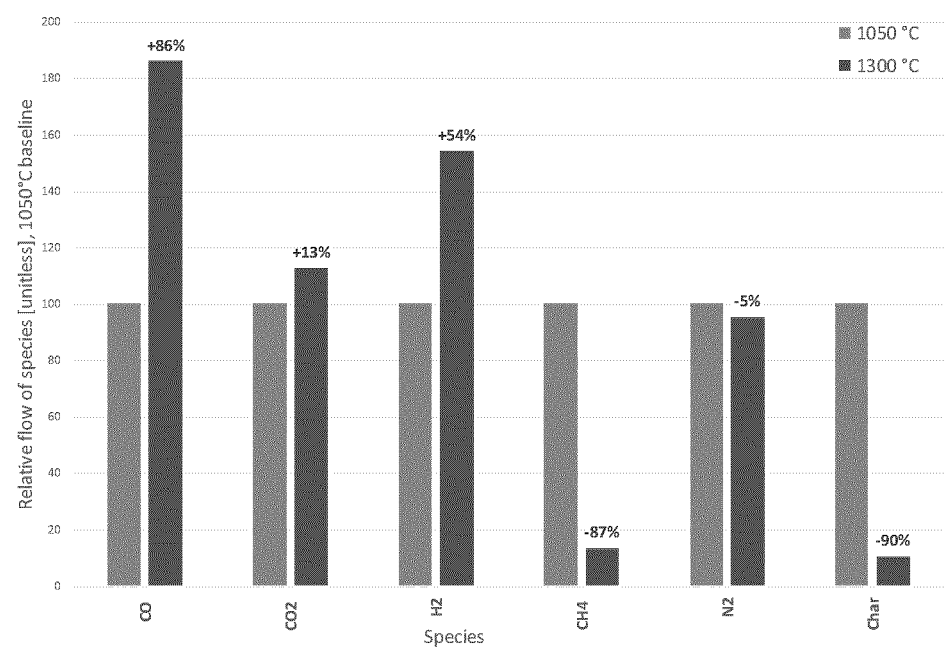
FIG. 7 illustrates a histogram showing the increased conversion to syngas performance from reforming at 1050° C. versus 1300° C.

At this point, the total carbon conversion to syngas reaches 90 to >99% conversion. The final syngas composition could vary depending on the operating temperature and feedstock/material 10 composition. It is thus provided a means to substantially increase the rate of conversion of the total carbon into syngas as illustrated in FIG. 7, wherein the rates of desired species CO, $CO_2$ and $H_2$ are substantially increased following the process described herein compared to the flow rate obtained of such species when the reforming is conducted for example at 1050° C. In addition, undesired species such as $CH_4$ are minimized.

The resulting syngas produced by the process described herein has low char, tar, HAP, phenol and other petroleum like by-products. The process provided has a high carbon conversion efficiency 90 to >99%, can handle coarse fluffy, fine fluffy or course to finely ground materials. Additionally, said process can handle molten minerals, optimizes the size/density of the feedstock preparation for the high temperature gasification zone and minimizes particle size/density range to optimize conversion and molten mineral flowability.

The carbonaceous materials encompassed herein can be biomass-rich materials which may be gasified in accordance with an embodiment, and include, but are not limited to, homogeneous biomass-rich materials, non-homogeneous biomass-rich materials, heterogeneous biomass-rich materials, and urban biomass. The carbonaceous material can also be plastic rich residues or any waste/product/gas/liquid/solid that include carbon. It may also be any type of coal and derivative such as pet coke, petroleum product & by-product, waste oil, oily fuel, hydrocarbon and tar.

Homogeneous biomass-rich materials are biomass-rich materials which come from a single source. Such materials include, but are not limited to, materials from coniferous trees or deciduous trees of a single species, agricultural materials from a plant of a single species, such as hay, corn, or wheat, or for example, primary sludge from wood pulp, and wood chips. It may also be materials from refined single source like waste cooking oil, lychee fruit bark or stillage from corn to methanol by-product.

Non-homogeneous biomass-rich materials in general are materials which are obtained from plants of more than one species. Such materials include, but are not limited to, forest residues from mixed species, and tree residues from mixed species obtained from debarking operations or sawmill operations.

Heterogeneous biomass-rich materials in general are materials that include biomass and non-biomass materials such as plastics, metals, and/or contaminants such as sulfur, halogens, or non-biomass nitrogen contained in compounds such as inorganic salts or organic compounds. Examples of such heterogeneous biomass-rich materials include, but are not limited to, industrial wastes, recycling facilities rejects, automobile fluff and waste, urban biomass such as municipal solid waste, such as refuse derived fuel (RDF), solid recovered fuel, sewage sludge, tire, synthetic textile, carpet, synthetic rubber, expended polystyrene, poly-film floc, etc. of fossil or vegetal origin, used wood utility poles and wood railroad ties, which may be treated with creosote, pentachlorophenol, or copper chromium arsenate, and wood from construction and demolition operations which may contain one of the above chemicals as well as paints and resins.

In an embodiment, carbonaceous materials can be fed as low density fluff RDF by a feeding system, lowering the costs of the pre-treatment of the feedstock by only partially pre-treating the RDF fluff. In another embodiment, carbonaceous materials can be a mixture of low density fluff having a particle size ranging from a few millimeters to many centimeters. In a non-limiting embodiment, carbonaceous materials can be in high density pelletized form with or without low density fluff. In another non-limiting embodiment, carbonaceous materials can be a solid, liquid, gas or any composition in any proportion thereof that contain the carbon atom.

In an embodiment, as encompassed herein, the reforming operating temperature is of about 1200° C. to about 2000° C. Accordingly, the thermal reforming temperature is above mineral melting point, such as for example of about 1200-1800° C., which increases syngas and ultimately alcohol yield. At 1300-1500° C., the thermal reforming as described herein provides virtual complete conversion of carbonaceous species to CO, $H_2$, $CO_2$ and $H_2O$, wherein the final syngas composition is driven by a Water Gas Shift (WGS) equilibrium.

While using a fluidized gasifier and cut sizing device as described and encompassed herein, the thermal reforming, as described herein at temperature above 1200° C. allows syngas conversion and yield to increase, with virtual complete conversion of methane, tar and aromatic tars (NBTX; naphthalene, benzene, toluene and xylene), wherein residual char/unconverted carbon is reduced.

Compared to a gasification as described in U.S. Pat. No. 8,137,655, wherein reforming is performed to at most 1200° C., mainly at about 1000° C., the process described herein allows decreasing substantially the amount of residual char as reported in FIG. 7.

The process described herein allows achievement of a high carbon to syngas conversion rate of at least 78% to 96%.

The syngas at the outlet of the thermal reformer 20 contains $H_2$, CO, $CO_2$ and $H_2O$. After additional processing as described below, the resulting clean syngas produced by the process described herein can then be subjected to further processing and conversion into other useful products such as a chemical. Particularly, it is encompassed that the process described herein produces for example fuel, preferably liquid fuel as well as a number of renewable chemicals. Examples of chemicals encompassed herein include methanol (MeOH), ethanol (EtOH), methyl acetate (MeOAc) and ethyl acetate (EtOAc), as described for example in WO 2013/188949 and WO 2013/091067, the content of which are incorporated herein by reference.

Typically the cleaning stages 24 of the reformed syngas process to produce clean syngas consists of sulfur removal, ammonia removal, chlorine removal, particle removal, carbon dioxide removal and other low trace catalyst poison removal steps. Typical process steps encompassed herein are for example wet water scrubbers, acid gas scrubbers and solid phase guard beds.

Acid gases produced at the end of the process described hereinabove mainly consist of carbon dioxide and hydrogen sulfide ($H_2S$). The syngas needs to be cleaned of those acid gases to protect the downstream catalysts from sulfur poisoning and to meet the optimal $CO_2$ purity for reuse in the process. The acid gas removal can be achieved using an acid gas removal (AGR) loop consisting of a countercurrent absorption using a regenerative methanol solvent in an absorption column. Alternatively, other systems can by used for acid gas removal, such as amine scrubbers, Selexol process, Purisol process, propylene carbonate solvent, etc.

As described herein, the AGR allows the removal of $H_2S$ and $CO_2$ from the syngas, in addition to other traces of sulfurous and nitrogenous compounds, i.e. carbonyl sulfide, carbon disulfide, etc. At the outlet of the absorption column, syngas is composed mainly of CO, $H_2$, with some of $CO_2$, and traces of sulfur compounds and it is sent to a syngas guard bed to remove the remaining sulfur compounds, as well as carbonyls and arsine, which are poisonous to synthesis catalysts and can reduce their active life significantly.

As described hereinabove, the process described herein can be subjected to further processing and encompassed is the conversion of syngas into chemicals. In an embodiment, the clean syngas may be reacted in the presence of a catalyst to produce methanol.

The clean syngas is then fed into a methanol reactor. Typically, a methanol reactor comprises a catalyst, such as for example a copper oxide (CuO) catalyst and/or a zinc oxide (ZnO) catalyst, where hydrogen, carbon monoxide and carbon dioxide combine at the surface of the catalyst and are transformed into methanol, as per the following main reactions:

$$CO+2H_2 \leftrightarrow CH_3OH$$

$$CO_2+H_2 \leftrightarrow CO+H_2O$$

$$CO_2+3H_2 \leftrightarrow CH_3OH+H_2O$$

Typically, the syngas enters the methanol reactor at 200° C. to 230° C. In an embodiment, the hydrogen, carbon monoxide and carbon dioxide are reacted at a temperature from about 100° C. to about 300° C. Hydrogen and carbon monoxide from the syngas are reacted at a pressure from about 250 to about 2 000 psi.

As an example, in ethanol production processes, the methanol produced from the methanol reactor can be further reacted with carbon monoxide in a carbonylation reactor to produce methyl acetate as per the following reaction:

$$CH_3OH+CO \leftrightarrow CH_3OOH \quad \text{(carbonylation reaction)}$$

$$CH_3OOH+CH_3OH \leftrightarrow CH_3COOCH_3+H_2O \quad \text{(esterification reaction)}$$

Depending on the carbonylation reactor integration, excess acetic acid ($CH_3COOH$) can be esterified in a separate reaction zone.

The methyl acetate produced is then fed into an hydrogenolysis reactor wherein the methyl acetate and hydrogen react to form ethanol and methanol as per the following reaction:

$$CH_3COOCH_3+2H_2 \leftrightarrow CH_3CH_2OH+CH_3OH$$

Particularly, carbon monoxide and hydrogen for the carbonylation and hydrogenolysis reactors above are obtained from a syngas separation step to generate a CO rich stream and an $H_2$ rich stream which can be used in their respective reactors. Such syngas separation step includes, for example known, membrane separation technology and/or cryogenic CO separation, etc.

As described herein, the generated syngas can be used for further processing into methanol and/or ethanol production. Alternatively, the generated syngas can be used for power and/or heat generation, hydrocarbon or drop-in fuel production (ex. using known Fischer-Tropsch process), higher alcohol and/or chemicals production.

While the present disclosure has been described in connection with specific embodiments thereof, it will be understood that it is capable of further modifications and this application is intended to cover any variations, uses, or adaptations, including such departures from the present disclosure as come within known or customary practice within the art and as may be applied to the essential features hereinbefore set forth, and as follows in the scope of the appended claims.

What is claimed is:

1. A method of converting a carbonaceous material into synthesis gas comprising:
   a) gasifying the carbonaceous material in a fluidized bed, producing a crude syngas;
   b) classifying the crude syngas by particle aerodynamic velocity into a cut sizing device producing classified crude syngas comprising classified particles with a range of particle diameter and density;
   c) introducing said classified particle crude syngas into a thermal reformer; and
   d) reforming said classified crude syngas at a temperature above mineral melting point, producing the synthesis gas.

2. The method of claim 1, wherein the cut sizing device is a freeboard enlargement, a cyclone, a perforated shroud, a helical strakes, a longitudinal slats, a filter, a cascade impactor, an aerodynamic classifier or any combination thereof.

3. The method of claim 1, wherein the carbonaceous material is fed to the fluidized bed reactor by a feeding system.

4. The method of claim 1, wherein a fluidizing agent is used to heat up the fluidized bed reactor and feed oxygen to gasification of the carbonaceous material.

5. The method of claim 4, wherein the fluidizing agent is air, oxygen, carbon dioxide, nitrogen, steam or any combination thereof.

6. The method of claim 1, wherein the carbonaceous material is gasified at a temperature of about 450° C. to about 800° C.; or about 500° C. to about 700° C.

7. The method of claim 1, wherein the classified particle crude syngas is reformed in a thermal reformer.

8. The method of claim 1, wherein the reforming operating temperature is of about 1200° C. to about 2000° C.

9. The method of claim 8, wherein air, oxygen, carbon dioxide, nitrogen, steam or any combination in any proportion thereof is fed to the reformer to increase the temperature of said reformer.

10. The method of claim 1, wherein the classified crude syngas is reformed at a temperature of about 1200° C. to about 1800° C.

11. The method of claim 1, wherein the reformer comprises a cooling wall membrane.

12. The method of claim 11, wherein the cooling wall membrane is made of studded pipes.

13. The method of claim 1, wherein the carbonaceous material is converted into syngas with at least 78% of carbon conversion rate; at least 90% of carbon conversion rate; or at least 96% of carbon conversion rate.

14. The method of claim 1, wherein the carbonaceous material is a liquid, a solid and/or a gas containing carbon.

15. The method of claim 1, wherein the carbonaceous material is a biomass.

16. The method of claim 15, wherein the biomass is an homogeneous biomass, a non-homogenous biomass, a non-homogeneous biomass, a heterogeneous biomass, urban biomass, or a combination thereof.

17. The method of claim 16, wherein the homogenous biomass is from a coniferous tree, a deciduous tree, an agricultural material, a primary sludge, waste cooking oil, lychee fruit bark or stillage; or wherein the non-homogenous biomass is from mixed forest residues, or mixed tree residues.

18. The method of claim 1, wherein the carbonaceous material comprises a plastic, a metal, an inorganic salt, an organic compound, industrial wastes, recycling facilities rejects, automobile fluff, municipal solid waste, ICI waste, C&D waste, refuse derived fuel (RDF), solid recovered fuel, sewage sludge, used wood utility poles, wood railroad ties, wood, tire, synthetic textile, carpet, synthetic rubber, materials of fossil fuel origin, expanded polystyrene, poly-film floc, construction wood material, or any combination thereof.

* * * * *